United States Patent
Allen et al.

(10) Patent No.: US 8,244,488 B2
(45) Date of Patent: Aug. 14, 2012

(54) THERMAL INSPECTION SYSTEMS

(75) Inventors: Jason Randolph Allen, Niskayuna, NY (US); Jared Michael Crosby, Scotia, NY (US); Christopher Joseph Uhl, Cincinnati, OH (US); Michael Orlando Cimini, Cincinnati, OH (US); Bianca Mary McCartt, Cincinnati, OH (US); James Walter Caddell, Milford, OH (US); Jared Reece Reynolds, Fort Thomas, KY (US); Robert William Tait, Niskayuna, NY (US); Andrew Frank Ferro, West Chester, OH (US)

(73) Assignee: General Electric Company, Niskayuna, NY (US)

( * ) Notice: Subject to any disclaimer, the term of this patent is extended or adjusted under 35 U.S.C. 154(b) by 287 days.

(21) Appl. No.: 12/731,405

(22) Filed: Mar. 25, 2010

(65) Prior Publication Data
US 2011/0125423 A1    May 26, 2011

Related U.S. Application Data

(60) Provisional application No. 61/264,384, filed on Nov. 25, 2009.

(51) Int. Cl.
G01F 1/34 (2006.01)
G01N 25/00 (2006.01)
G06F 15/00 (2006.01)
(52) U.S. Cl. .................. 702/47; 73/204.13; 374/121
(58) Field of Classification Search .............. 702/45, 702/47, 100; 73/204.13, 861.04, 861.05; 374/25, 121
See application file for complete search history.

(56) References Cited

U.S. PATENT DOCUMENTS

| | | | |
|---|---|---|---|
| 4,067,237 A | 1/1978 | Arcella | |
| 4,621,929 A | 11/1986 | Phillips | |
| 4,644,162 A | 2/1987 | Bantel et al. | |
| 4,777,368 A | 10/1988 | Kerlin, Jr. | |
| 4,896,281 A | 1/1990 | Mack | |
| 5,111,046 A | 5/1992 | Bantel | |
| 5,328,331 A | 7/1994 | Bunker et al. | |
| 5,719,341 A * | 2/1998 | Reynolds et al. | 73/861.95 |
| 5,750,454 A | 5/1998 | Shimizu et al. | |
| 6,422,743 B1 | 7/2002 | Nirmalan et al. | |
| 6,517,236 B2 | 2/2003 | Sun et al. | |

(Continued)

OTHER PUBLICATIONS

J.R. Allen et al., "Thermal Inspection System and Method Incorporating External Flow," U.S. Appl. No. 12/683,638, filed Jan. 7, 2010.

(Continued)

*Primary Examiner* — Bryan Bui
(74) *Attorney, Agent, or Firm* — Penny A. Clarke

(57) ABSTRACT

A thermal inspection system includes a fluid source configured to supply a warm flow and a cool flow, indirectly or directly, to internal passage(s) of a component. The system includes an imager configured to capture a time series of images corresponding to a transient thermal response of the component to the warm and cool flows. The system further includes at least one flow meter configured to measure the warm and cool flows supplied to the component and a processor operably connected to the imager. The processor determines the transient thermal response of the component around a transition time. The flow supplied to the component switches from the warm flow to the cool flow at the transition time. The processor compares the transient thermal response around the transition time with one or more baseline values or with an acceptable range of values to determine if the component meets a desired specification.

22 Claims, 5 Drawing Sheets

U.S. PATENT DOCUMENTS

| | | | |
|---|---|---|---|
| 6,517,238 | B2 | 2/2003 | Sun et al. |
| 6,570,175 | B2 | 5/2003 | Bales et al. |
| 6,585,408 | B2 | 7/2003 | El-Gabry et al. |
| 6,711,506 | B2 | 3/2004 | Bales et al. |
| 6,732,582 | B2 | 5/2004 | Bunker et al. |
| 6,796,709 | B2 | 9/2004 | Choi |
| 6,804,622 | B2 | 10/2004 | Bunker et al. |
| 6,984,100 | B2 | 1/2006 | Bunker et al. |
| 7,040,805 | B1 | 5/2006 | Ou et al. |
| 7,388,204 | B2 | 6/2008 | Key et al. |
| 7,651,261 | B2 | 1/2010 | Bunker et al. |
| 2002/0001185 | A1 | 1/2002 | Wilhelm et al. |
| 2003/0128736 | A1 | 7/2003 | Dalio et al. |
| 2004/0225482 | A1 | 11/2004 | Vladimirov et al. |
| 2006/0256837 | A1 | 11/2006 | Clifton et al. |
| 2009/0016402 | A1 | 1/2009 | Bunker et al. |
| 2009/0297336 | A1 | 12/2009 | Allen et al. |

OTHER PUBLICATIONS

R. S. Bunker et al., "Method for Quantifying Hole Flow Rates in Film Cooled Parts," U.S. Appl. No. 12/413,756, filed Mar. 30, 2009.

A. Daniels, "Nondestructive pulsed infrared quantitative evaluation of metals,", Thermosense XVIII: AN international Conference on Thermal Sensing and Imaging Diagnostic Applications, Apr. 10-12, 1996, vol. 2766, pp. 185-201.

"Thermography Inspection System for Gas Turbine Blades," 7th ECNDT, Copenhagen, May 1998. 8 pages.

M. Lin et a., "A Transient Liquid Crystal Method Using Hue Angle and a 3-D Inverse Transient Conduction Scheme," ASM Gas Turbines Materials Technology Conference, Oct. 12-15, 1998, 7 pages.

JP1201165 Abstract, Aug. 14, 1989.

S. Friedrichs, "Endwall Film-Cooling in Axial Flow Turbines," Whittle Laboratory, Jan. 1997, 206 pages.

R. S. Bunker et al., "The Determination of in-Situ Film Hole Flow Rates Using a Transient Thermal Inertia Method," Proceeding of ASME Turbo Expo 2003, Jun. 16-19, 2003, GT2003-38610.

N. V. Nirmalan et al., "The Measurement of Full-Surface Internal Heat Transfer Coefficients for Turbine Airfoils Using a Nondestructive Thermal Inertia Technique," Journal of Turbomachinery, vol. 125, Jan. 2003. pp. 83-89.

J. J. Stiglich, Jr. et al., "The Thermal Inertia Analysis Technique in Gas Turbine Component Reliability Assessment," Oct. 12-15, 1998, pp. 138-144.

R. D. Rosemau et al., "Aircraft Engine Blade cooling Holes Detection and Classification from Infrared Images," SPIE Conference on Nondestructive Evaluation of Aging Aircraft, vol. 3586, No. 85, Mar. 1999.

Search Report, Feb. 16, 2011.

K. Ding, "Test of jet engine turbine blades by thermography," Optical engineering, Nov./Dec. 1985, vol. 24, No. 6, pp. 1055-1059.

* cited by examiner

THERMAL INSPECTION SYSTEMS

CROSS REFERENCE TO RELATED APPLICATIONS

This application claims the benefit of U.S. Provisional Patent Application, Ser. No. 61/264,384, filed Nov. 25, 2009 and entitled "Thermal inspection system and method," which is incorporated herein by reference in its entirety.

BACKGROUND

The invention relates generally to thermal inspection systems and methods and more specifically, to non-destructive thermal inspection of cooled parts.

Hot gas path components, such as turbine airfoils, employ advanced cooling techniques, such as film cooling, as well as advanced coatings, such as thermal barrier coatings (TBCs), in order to withstand their extremely high operating temperatures. Film cooled components are typically inspected manually using pin checks, which involve the use of undersized pin gauges, and/or by water flow visualization, which involves flowing water through the component and having an operator visually verify that the water is flowing from each cooling hole. These manual approaches are qualitative and subject to operator interpretation.

Infrared (IR) inspection techniques have the potential to perform quantitative, objective inspection of film cooled components. However, IR inspection systems and current airflow check systems typically have conflicting requirements, thereby necessitating the use of separate systems, at considerable expense. Further, existing IR inspection systems are often limited to the inspection of uncoated parts.

It would therefore be desirable to develop a combined IR inspection and airflow check system. It would further be desirable for the inspection system to be capable of inspecting coated parts, for example of inspecting hot gas path components with TBCs.

BRIEF DESCRIPTION

One aspect of the invention resides in a system for thermal inspection of a component having at least one cooling hole. The system includes a fluid source configured to supply a warm flow and a cool flow, indirectly or directly, to at least one internal passage of the component. The system further includes an imager configured to capture a time series of images corresponding to a transient thermal response of the component to the warm and cool flows. The thermal response corresponds to a number of intensity or temperature values for an external surface of the component. The system further includes at least one flow meter configured to measure the warm and cool flows supplied to the component and a processor operably connected to the imager. The processor is configured to determine the transient thermal response of the component around a transition time. The flow supplied to the component switches from the warm flow to the cool flow at the transition time. The processor is further configured to compare the transient thermal response around the transition time with one or more baseline values or with an acceptable range of values to determine if the component meets a desired specification.

Another aspect of the invention resides in a system for thermal inspection of a component having a number of cooling holes and a number of internal passages. The system includes a plenum, in fluid communication with at least one of the internal passages of the component, and a fluid source configured to supply a warm flow and a cool flow to the plenum. The system further includes at least one flow meter configured to measure a mass flow rate for the warm and cool flows supplied to the plenum and an imager configured to capture a time series of images corresponding to a transient thermal response of the component to the warm and cool flows. The thermal response corresponds to a number of intensity or temperature values for an external surface of the component. The system further includes a number of actuated air flow stops configured to selectively interrupt the fluid communication between the plenum and respective internal passages and a processor operably connected to the imager. The processor is configured to determine the transient thermal response of the component around a transition time. The flow supplied to the component switches from the warm flow to the cool flow at the transition time. The processor is further configured to compare the transient thermal response around the transition time with one or more baseline values or with an acceptable range of values to determine if the component meets a desired specification.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
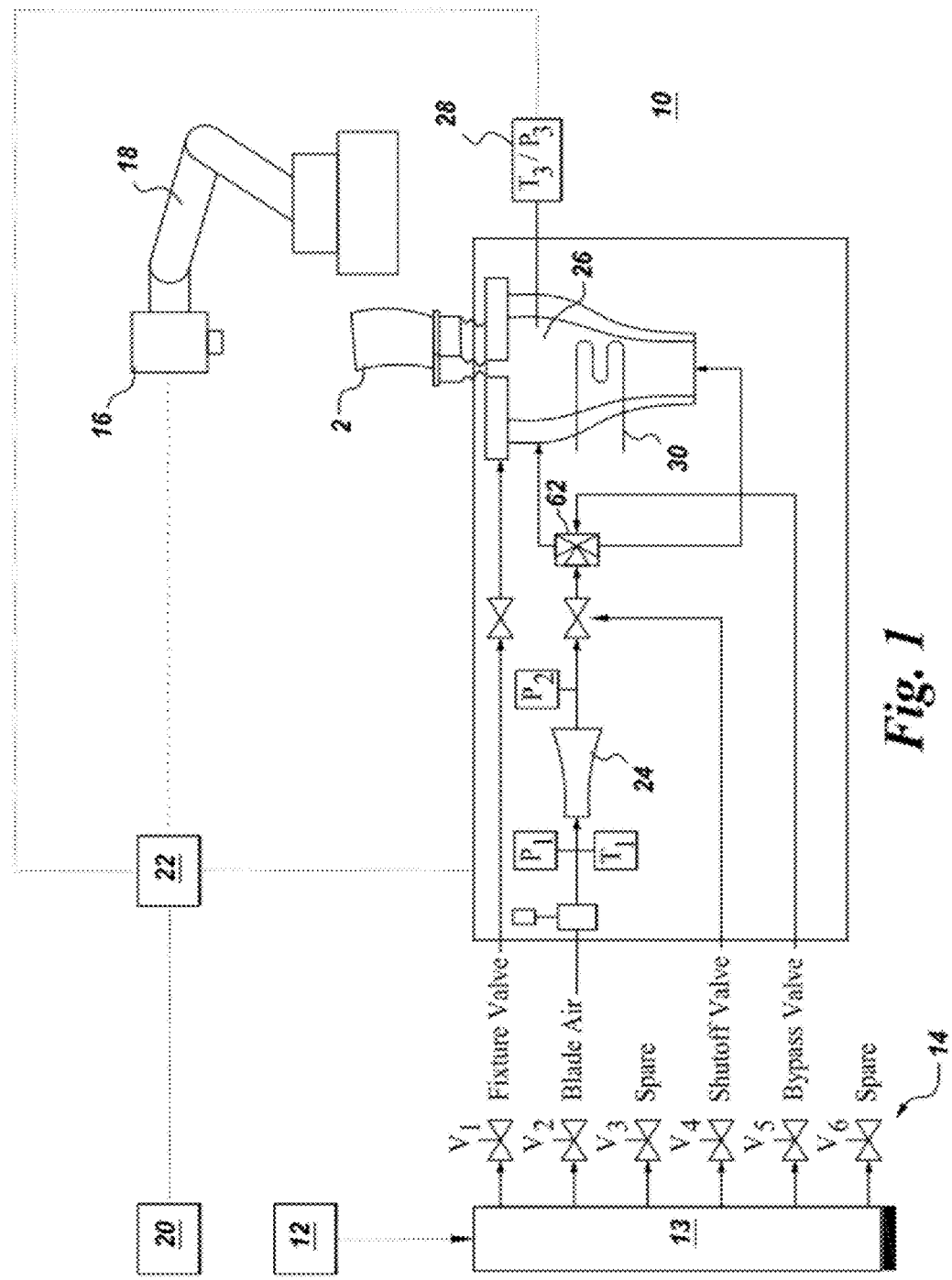
FIG. 1 illustrates a thermal inspection system embodiment of the invention.

An inspection system for thermal inspection of a component 2 having at least one cooling hole is described with reference to FIG. 1. As indicated in FIG. 1, the thermal inspection system 10 includes a fluid source 12 configured to supply a warm flow and a cool flow, indirectly or directly, to at least one internal passage of the component 2. As used herein, the term "fluid" should be understood to encompass liquids and gases. Example fluids include compressed gases, such as compressed air. Other non-limiting examples of the fluid include nitrogen, steam, water and any Newtonian fluid. It should be noted that, as used herein, the terms "warm" and "cool" are merely relative. Example 'components' include equipment used in engine systems such as, but not limited to, turbine engines. Non-limiting examples of components include film cooled components, such as hot gas path components in turbines, for example stationary vanes (nozzles), turbine blade (rotors), combustion liners, other combustion system components, transition pieces, and shrouds. For the example arrangement shown in FIG. 1, the fluid source includes an air source 12 (for example a compressor) and a manifold 13 and associated valving 14. The actuation of the flow can be sudden or gradual. However, according to a particular embodiment, the flow rate remains substantially steady during the time period of usable data, thereby providing a "steady-flow thermal transient" during this time period.

The system further includes an imager 16 configured to capture a time series of images corresponding to a transient thermal response of the component 2 to the warm and cool flows. For example, a series of images may be captured in succession over a period of time to obtain a thermal profile of a number of surface locations on the part as a function of time. The thermal response corresponds to a number of intensity or temperature values for an external surface of the component 2. It should be noted that the thermal response is typically obtained as a set of intensity values for the images. The intensity values can be correlated with temperature values to determine the temperature. Although the operations described herein as described as being performed on temperature values, one skilled in the art will recognize that operations may be carried out with the intensity values. A number of imagers 16 may be employed, including but not limited to, infrared detection devices such as infrared cameras, actuating pyrometers, and single point pyrometers. According to a particular embodiment, the imager comprises an infrared camera. One non-limiting example of an infrared camera is a ThermCAM® SC3000 infrared imaging camera, which is commercially available from FLIR Systems, with offices in Portland, Oreg., Boston, Mass., and Stockholm, Sweden.

In addition, the thermal inspection system 10 may further comprise a manipulator 18 configured to control and automate movement of the imager 16 and/or component 2 relative to the other. The manipulator 18 may comprise a robotic arm or other automation means. The thermal inspection system 10 may further include a display monitor 20 coupled to the processor 22 to display the results of the thermal inspection.

The thermal inspection system 10 further includes at least one flow meter 24 configured to measure the warm and cool flows supplied to the component 2. Depending on the specific implementation, the flow may switch from heating to cooling or from cooling to heating. Non-limiting examples of flow meters 24 include sonic nozzles, Coriolis meters, laminar flow meters, orifice plates, and subsonic Venturis.

The thermal inspection system 10 further includes a processor 22 operably connected to the imager 16 and configured to determine the transient thermal response of the component 2 around a transition time, wherein the flow supplied to the component 2 switches from the warm flow to the cool flow at the transition time. As used herein, the phrase "around the transition time" should be understood to mean times near or at the transition time. For example, the time at which the transient thermal response is determined may be within a range of +/−0.010 of the transition time. The processor 22 is further configured to compare the transient thermal response around the transition time with one or more baseline values or with an acceptable range of values to determine if the component 2 meets a desired specification. Non-limiting examples of the baseline values include: one or more local values, mean value of a group of local values and a standard deviation of a group of local values. Moreover, "baseline values" can be extracted, for example, using sample (or "nominal") parts that meet the desired specifications. For example, the baseline value may be determined by measuring a baseline transient thermal response of a sample component known to have properly sized, unblocked cooling passages. Non-limiting examples of the phrase 'meets a desired specification' include: avoiding partial or total blockage from deposits that may build up on an exterior surface of the component resulting in a partial or total blockage of the hole from outside; having the correct film hole size; avoiding an improper formation of the passage such as left over slag from a casting operation, debris from cleaning processes; and avoiding improper dimensions that result in a partial or total blockage of the internal passage.

The processor 22 may also be coupled to the camera controller (not shown) and output results obtained on the display monitor 20. The processor is typically capable of capturing an image frame rate of adequate frequency, for example greater than 10 frames per second and typically greater than 15 frames per second, from the imager. The temperature-time history of the component 2 is readily measured by the use of the imager 16 and the processor 22. The temperature-time history of each location on an external surface of the component 2 may be recorded in the processor 22 for analysis. Detailed measurement of the external surface temperature distribution is dependent on the resolution of the imager 16, i.e. the density of a pixel array in the imager 16.

It should be noted that the present invention is not limited to any particular processor for performing the processing tasks of the invention. The term "processor," as that term is used herein, is intended to denote any machine capable of performing the calculations, or computations, necessary to perform the tasks of the invention. The term "processor" is intended to denote any machine that is capable of accepting a structured input and of processing the input in accordance with prescribed rules to produce an output. It should also be noted that the phrase "configured to" as used herein means that the processor is equipped with a combination of hardware and software for performing the tasks of the invention, as will be understood by those skilled in the art.

According to particular embodiments, the processor 22 is configured to determine the transient thermal response by interrogating a second derivative of the intensity or temperature values with respect to time around the transition time. Alternatively, frame number can be correlated back to time with the frame rate. The processor 22 is configured to perform the comparison by comparing the second derivative of the intensity or temperature values with the respective baseline value(s) or with the respective acceptable range of values to determine if the component meets the desired specification.

According to a more particular embodiment, each of the images corresponds to a number of pixels, and the processor 22 is further configured to identify respective locations of the cooling holes on the external surface of the component 2 based on the relative intensities of the pixels in the images. For certain example embodiments, the processor 22 is further configured to determine a minimum for the second derivative and to compare a magnitude of the minimum with the one or more baseline values or with the acceptable range of values to determine if a respective cooling hole is at least partially blocked. Namely, within this data subset the "peak" value (a negative value and thus a minima) is determined. As the component heats up, it experiences a fairly constant rate of increasing temperature (T'). When the heater 30 is shut off and cool air simultaneously bypassed around the heater 30, the rate of temperature change with respect to time (or slope) changes abruptly. By taking the second derivative of temperature (or intensity), the change in slope or acceleration of temperature (or intensity) for the cooling hole can be quantified.

With an open cooling hole, the second derivative peak magnitude at the transition from hot to cool air is generally a high absolute value. Factors, such as where the film hole is located along the internal passage, can affect this generalization. For example, cooling holes at the end of an internal serpentine passage experience a weaker thermal transient than those located at the inlet. This is due to the air losing heat to the bulk material during the hot air transient as well as the air picking up heat during the cooling transient. Thus, each cooling hole has a unique response to the thermal transient that must be characterized. Initial testing found that one indicator of a blocked cooling hole is a reduction in the peak absolute value of θ" at the point of transition from hot to cold air. A blocked cooling hole loses the additional cooling benefit of convection and relies only on conduction, thus experiencing reduced temperature acceleration compared to an open cooling hole.

In accordance with another particular embodiment, the processor 22 is further configured to determine a minimum for the second derivative and to compare a time at which the minimum occurs with the baseline value(s) or with the acceptable range of values to determine if a respective cooling hole is at least partially blocked.

According to a particular embodiment, each of the images corresponds to a number of pixels, and the processor 22 is further configured to compute a first derivative T'(t) of the intensity or temperature values with respect to time for at least a subset of the pixels and to normalize the first derivative T'(t) of the intensity or temperature values with respect to time for the subset of the pixels. For example, this first derivative may be normalized according to Eq. 1 to account for day-to-day variation in inlet air temperature and varying initial part temperatures.

$$\theta'(t) = \frac{T'(t) - T'_{min}}{T'_{max} - T'_{min}} \quad [\text{Eq. 1}]$$

Beneficially, normalization eliminates the effect of any day-to-day variation in inlet air temperature and varying initial part temperatures. For this embodiment, the processor 22 is further configured to use the normalized first derivative to compute the second derivative of the intensity or temperature values with respect to time, such that the second derivative is interrogated around the transition time at which the flow switches from the warm to the cool flow. Namely, another forward derivative is taken on θ'(t), and an average of the pixel values is calculated to represent the cooling hole at each time step. The resulting θ"(t) is then interrogated around the point where the heater 30 is turned off and flow is bypassed around the heater. Other processes may be employed to obtain a normalized second derivative. For example, T→θ→θ'→θ".

Figure 4:
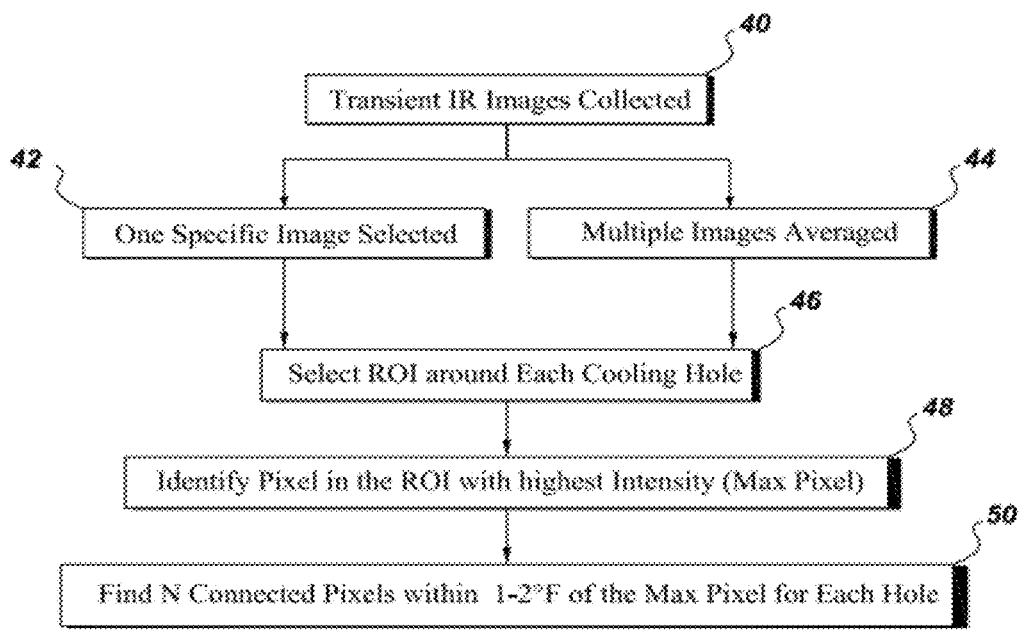
FIG. 4 illustrates an example process for identifying the location of the cooling holes.

The processor 22 may be further configured to identify respective locations of the cooling holes on the external surface of the component 2 based on the relative intensities of the pixels in the images. Non-limiting examples of the cooling holes include film-cooling holes. For this embodiment, the subset of the pixels selected for computation of the first derivatives corresponds to the locations of the cooling holes. For example, the processes shown in FIGS. 4 and 5 may be employed. However, these are examples, and the invention is not limited to these specific process maps. In the example process illustrated by FIG. 4, at step 40, transient IR images are collected. Next, either a specific image is selected at step 42 or multiple images are averaged at step 44. At step 46, a region of interest (ROI) is selected for a respective cooling hole using either the selected image or averaged image. At step 48, the pixel in the ROI with the highest intensity (max pixel) is selected. A number N of connected pixels within one to two degrees Fahrenheit of the max pixel are selected at step 50, and the resulting subset of pixels centered on the max pixel corresponds to the cooling hole. In one non-limiting example, N=5. This process can be performed for each of the cooling holes, in order to identify their locations.

Figure 5:
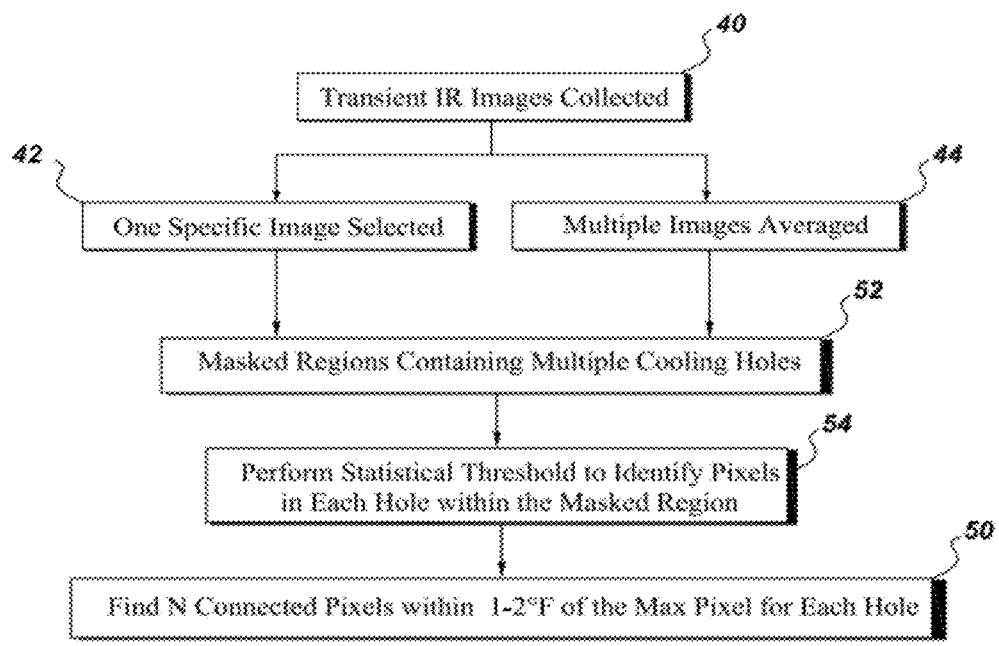
FIG. 5 illustrates another example process for identifying the location of the cooling holes.

Similarly, in the example process illustrated by FIG. 5, at step 40, transient IR images are collected. Next, either a specific image is selected at step 42 or multiple images are averaged at step 44. At step 52, bulk regions containing multiple cooling holes are masked. The bulk masking serves several purposes. First, the bulk masking narrows the region of interest and analysis to increase the probability of finding holes while minimizing the probability of selecting a "false hole" (or a blemish on the airfoil surface that appears to be a hole in the image). In addition, bulk masking utilises edges and other features to account for small image and holes shifts and thereby improves the software's ability to locate the holes accurately. Significantly, bulk masking allows for faster setup for new parts or new manufacturing/inspection lines. Moreover, the bulk masking enables the inspection of parts with larger hole population densities or holes that are more closely spaced. At step 54, a statistical threshold is performed to identify the pixels in each cooling holes within the masked region. One non-limiting example of a statistical threshold is adaptive thresholding. This operation uses an intensity gradient setting that will highlight features in an image by the rate of change in contrast from pixel to pixel. Although this is a common practice in image processing, it is not typically used for the analysis of thermal inspection data. Once these features (holes) are identified (usually as more than several pixels), the centroid of the identified feature is fed into Step 50. In addition, after the thresholding is performed, pattern recognition or other feature labeling/feature identification/mapping operating can take place. At step 50, a number N of connected pixels within one to two degrees Fahrenheit of the max pixel are selected, and the resulting subset of pixels centered on the max pixel corresponds to the respective cooling hole. In one non-limiting example, N=5. The process of FIG. 5 can be performed for each of the cooling holes, in order to identify their locations. As discussed above, the processor 22 may be further configured to determine a minimum for the second derivative and to compare either the magnitude of the minimum or the time at which the minimum occurs with the baseline value(s) or with the acceptable range of values to determine if a respective cooling hole is at least partially blocked.

A number of different components 2 have more than one cooling hole. According to a particular embodiment, the processor 22 is further configured to identify the location of any of the cooling holes that do not meet the desired specification. For example, the processor 22 may output the row and hole number for the blocked hole for the operator to view on the display 20. Alternatively, the processor 22 may direct a bar code labeler (not shown) to print a bar code that identifies the location of the blocked hole, so that the label (not shown) can be affixed to the component 2. The bar-code label can then be scanned, and the information encoded therein used to repair or rework the component 2.

For the arrangement shown in FIG. 1, the thermal inspection system 10 further includes a plenum 26 and at least one pressure sensor 28. As indicated, the fluid source 12 supplies the warm and cool flows to the plenum 26 via manifold 13 and valves 14. The flow meter(s) 24 and the pressure sensor(s) 28 are configured to measure the warm and cool flows and pressures supplied to the plenum 26. The plenum 26 is in fluid communication with at least one internal passage of the component 2. For the illustrated embodiment, at least one temperature sensor (also indicated by reference numeral 28) is provided to measure the temperature of the fluid supplied to the plenum. These flow rate, pressure and temperature readings can be used to ensure that there are consistent conditions for the measurements. Additionally, temperature and/or pressure sensors may be provided to measure the temperature/pressure at other points along the fluid flow path, as indicated by $P_1$, $P_2$ and $T_1$ in FIG. 1, for example.

For the arrangement shown in FIG. 1, the thermal inspection system 10 further includes at least one manipulator 18 for manipulating the relative position and/or the relative orientation of the imager 16 and the component 2. For the illustrated arrangement, the manipulator 18 comprises a robotic arm 18 configured to move the imager 16 relative to the component 2. For particular embodiments, the manipulator may have six degrees of freedom.

Figure 6:
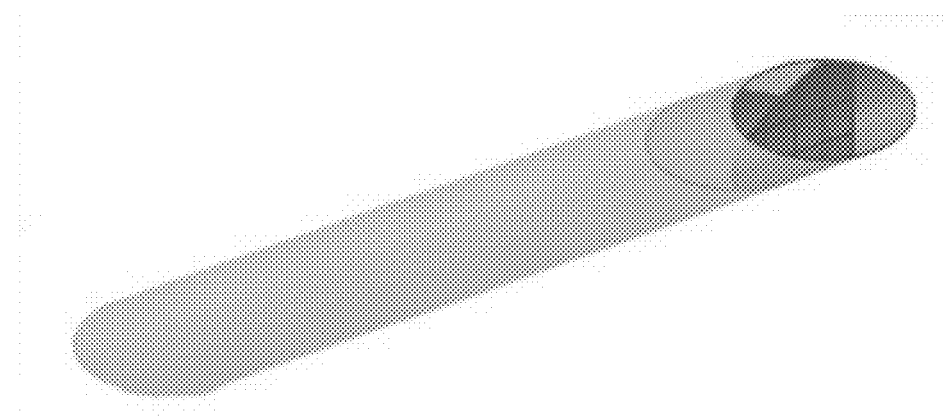
FIG. 6 shows a simple angled hole, and the red pixels represent the region imaged and analyzed.
Figure 7:
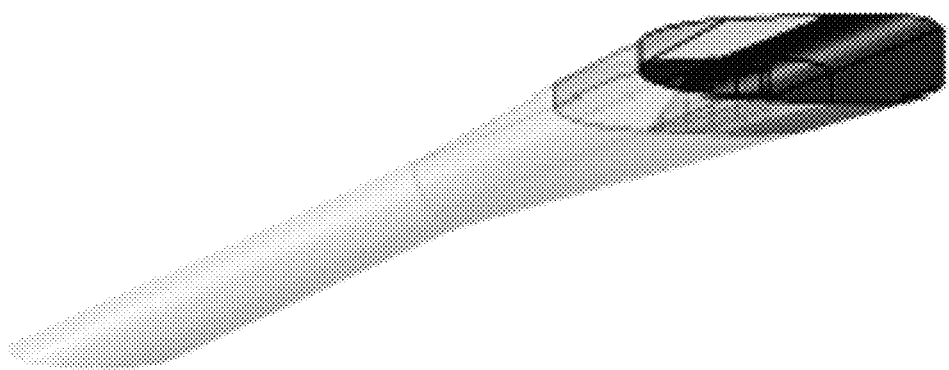
FIG. 7 depicts an example shaped (diffuser) hole, where the red pixels represent the region imaged and analyzed.

A number of different components 2 have more than one cooling hole. Example film cooling holes are depicted in FIGS. 6 and 7. The red and blue portions of the film holes shown in FIGS. 6 and 7 are the visible areas imaged by the IR camera. A simple angled hole is illustrated in FIG. 6, and the red pixels represent the region imaged and analyzed to determine the presence of an open or blocked film hole. FIG. 7 depicts an example shaped (diffuser) hole, where the red pixels represent the region imaged and analyzed to determine the presence of an open or blocked film hole. For particular embodiments, the manipulator 18 is configured to change the angle of the relative orientation of the imager 16 and the component 2 to inspect different cooling holes. In addition, the manipulator 18 may be configured to change the relative position of the imager 16 and the component 2 to adjust the focal point of the imager 16 within a respective cooling hole. This feature is particularly useful for inspecting shaped holes, one non-limiting example of which is shown in FIG. 7.

Figure 2:
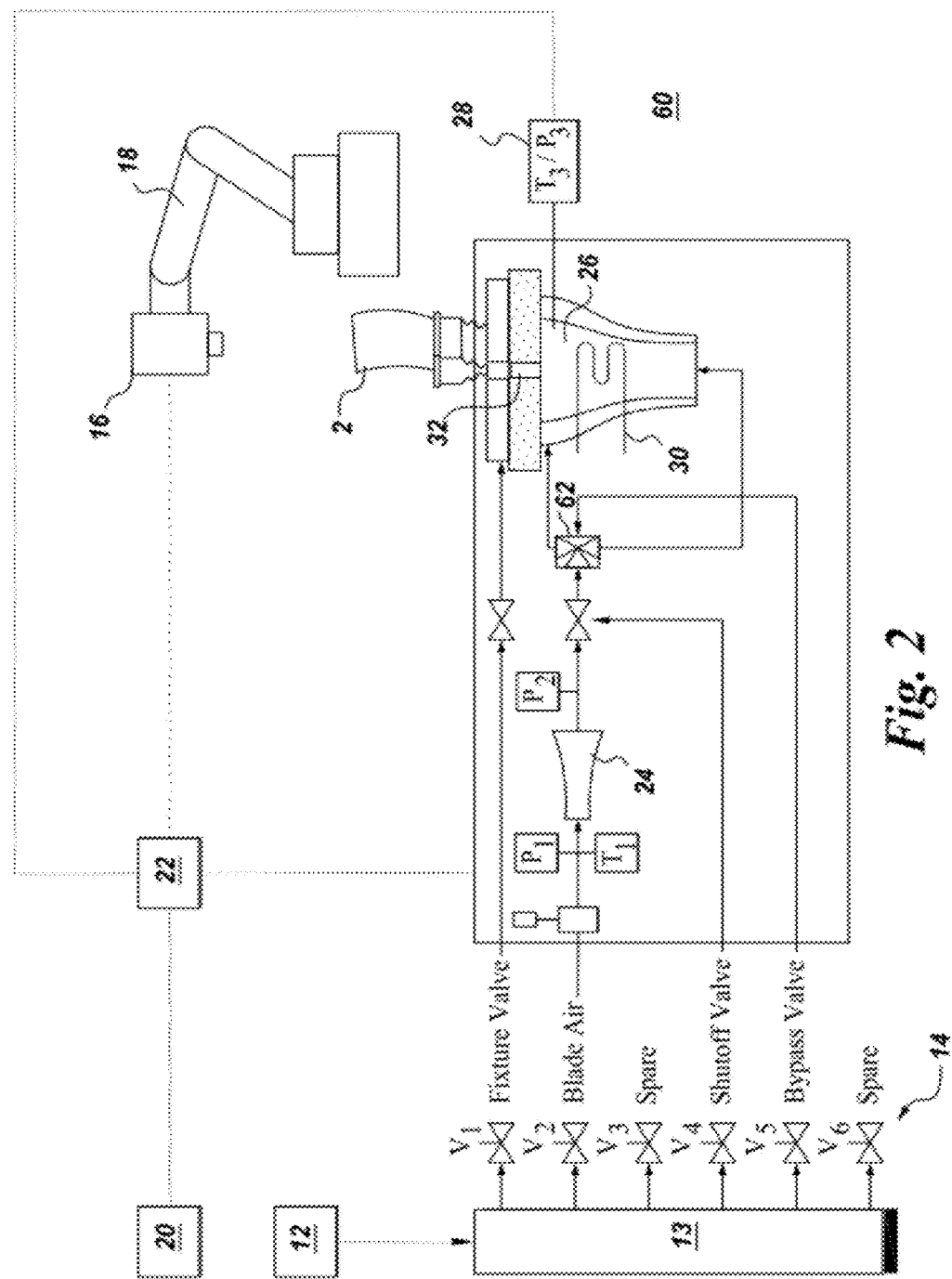
FIG. 2 illustrates a thermal inspection system with airflow checks embodiment of the invention.

Another embodiment of the invention directed to a thermal inspection system 60 with airflow checks is described with reference to FIG. 2. As is evident from FIGS. 1 and 2, a number of the features of thermal inspection system 60 are similar to those of thermal inspection system 10, and details of the common features are not repeated. Thermal inspection system 60 is particularly suited to inspecting components 2 with multiple cooling holes and multiple internal passages. As indicated in FIG. 2, the system 60 includes a plenum 26, in fluid communication with at least one of the internal passages of the component 2, and a fluid source 12 configured to supply a warm flow and a cool flow to the plenum 26. The plenum 26 and fluid source 12 are discussed above in detail with reference to FIG. 1.

Thermal inspection system 60 further includes at least one flow meter 24 configured to measure a mass flow rate for the warm and cool flows supplied to the plenum 26. Thermal inspection system 60 also includes an imager 16 configured to capture a time series of images corresponding to a transient thermal response of the component 2 to the warm and cool flows. The thermal response corresponds to a number of intensity or temperature values for an external surface of the component 2. The flow meter 24 and imager 16 are discussed above in detail with reference to FIG. 1.

For the illustrated example of FIG. 2, thermal inspection system 60 further includes a heater 30 for heating the fluid to be supplied to the internal passages and a bypass (or three-way) valve 62 for bypassing the heater 30. For this non-limiting arrangement, the hot and cold airstreams are separated. These airstreams are supplied by a single metered air source through plenum 26. The airflow is directed to the mesh heater 30 or bypassed around the heater 30 by a 3-way valve 62. The heater 30 and heater by-pass exhaust directly into plenum 26 before entering the component cooling passages.

As schematically depicted in FIG. 2, thermal inspection system 60 further includes a number of actuated air flow stops (collectively indicated by reference numeral 32) that are configured to selectively interrupt the fluid communication between the plenum 26 and respective internal passages. In one non-limiting example, the cooling passages in the component 2 are opened and closed to the plenum 26 by a series of actuated plugs 32. The plugs 32 cover the inlets to the component cooling passages and may be actuated by pneumatic cylinders (not shown). A tight seal may be achieved through an o-ring seal (not shown) thus preventing leakage into passages.

Similar to the arrangement shown in FIG. 1, the thermal inspection system 60 further includes a processor 22 operably connected to the imager and configured to determine the transient thermal response of the component around the transition time and compare the transient thermal response around the transition time with one or more baseline values or with an acceptable range of values to determine if the component meets a desired specification. According to a particular embodiment, the processor 22 is configured to determine the transient thermal response by interrogating a second derivative of the intensity or temperature values with respect to time around the transition time. For this embodiment, the processor is configured to perform the comparison by comparing the second derivative of the intensity or temperature values with the one or more baseline values or with the acceptable range of values to determine if the component 2 meets the desired specification. Typically, each of the images corresponds to a number of pixels, and for particular embodiments, the processor 22 is further configured to identify respective locations of the cooling holes on the external surface of the component 2 based on the relative intensities of the pixels in the images. Other aspects of the processor 22 are discussed above with reference to FIGS. 1, 4 and 5.

Beneficially, the thermal inspection system 60 may be used to detect film hole manufacturing defects in turbine blades or other hot gas path components before and/or after the components are coated. In one embodiment of the system 60, blocked film holes are identified. The component 2 is loaded into a fixture, which sits above a plenum 26. A series of automated steps lock the component and establish the desired air mass flow rate through the component. An infrared camera 16 mounted to a robotic arm 18 is positioned at various locations needed to inspect all the film holes on the component. The camera 16 is triggered to record the surface temperature response at each position as the component 2 undergoes a brief heating transient using a mesh heater 30, which provides an approximate step change in temperature as well as a cooling transient. The cooling transient occurs as the heater 30 is shut off while simultaneously a valve 62 bypasses cool air around the heater 30 to the plenum 26. Image processing algorithms are used to identify the pixels defining each film hole in the camera frame, as discussed above with reference to FIGS. 4 and 5, for example. The second derivative of the transient data of those pixels may then be analyzed around the start of the cooling transient to determine if the film hole is within acceptable tolerances. For particular embodiments, the system 60 documents any blocked film holes and displays a results summary to the operator on display 20.

In one non-limiting example implementation, a FLIR SC4000 infrared camera 16 with InSb detector is mounted to a FANUC LR Mate 200 iC 6 axis robotic arm 18. The robotic arm 18 is mounted to a base, which is fully enclosed with appropriate safety interlocks. The camera 16 nominally operates in the 3-5 micron wavelength range and has a filter (not shown), which further narrows the range to 3.9-5. The component 2 to be inspected is loaded into a standard air flow fixture, currently used to determine if components meet film hole air flow specifications, which seals the bottom of the component and allows air flow to the interior passages from a plenum 26 mounted underneath the base. Beneath the plenum 26 is a mesh heater 30 consisting of a Nichrome V wire mesh 30 connected to a DC power supply (not shown) with programmable logic, which controls the output power level and establishes the desired heating transient profile. A pneumatic three-way valve 62 actuated by a solenoid valve directs the flow of air to a diffuser located beneath the mesh heater or, when actuated, bypasses the air directly to the plenum. Upstream of the three-way valve 62 is a sonic nozzle 24 used to measure mass flow rate as well as a programmable air regulator to set the desired mass flow rate. For this particular example, LabVIEW software combined with data acquisition hardware is used to control all system components and timing through various analog and digital inputs/outputs.

For the illustrated arrangement, the thermal inspection system 60 further includes at least one pressure sensor for measuring the pressure within the plenum 26 and at least one temperature sensor for measuring the temperature of the fluid within the plenum 26. Both the temperature and pressure sensor are indicated by reference numeral 28 in FIG. 2. For the illustrated arrangement, the processor 22 is operatively connected to the pressure and temperature sensors 28 and to the flow meter 24, and the processor 22 is further configured to determine a flow rate though at least one of the internal passages based on the pressure and temperature within the plenum 26 and on the mass flow rate measured by flow meter 24.

Figure 3:
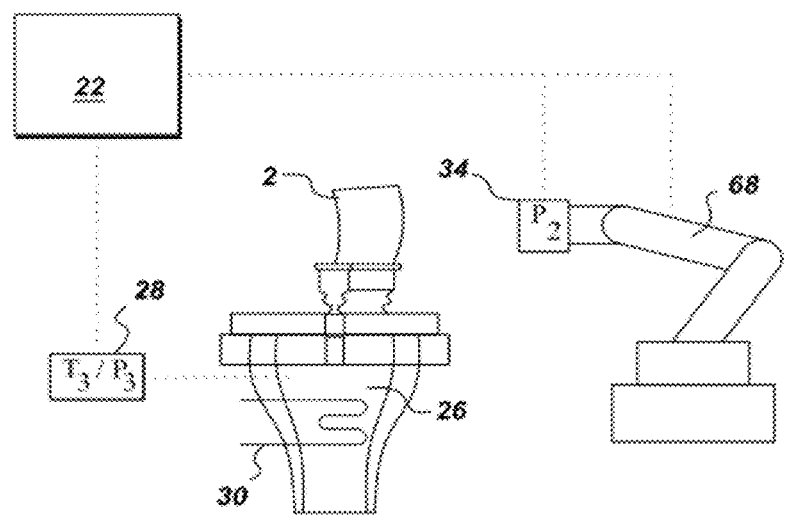
FIG. 3 illustrates optional aspects of the thermal inspection system shown in FIG. 2.

FIG. 3 illustrates an additional, optional feature for thermal inspection system 60. For the arrangement shown in FIG. 3, the thermal inspection system 60 further includes at least one pressure transducer 34 configured to block a respective one of the cooling holes and to measure a static pressure at the cooling hole. According to a more particular embodiment, the processor 22 is operably connected to the pressure transducer 34 and is further configured to compare the measured static pressure with a baseline value to determine whether the respective cooling hole is operable. For the arrangement shown in FIG. 3, the system 60 further includes at least one manipulator 68 operatively connected to the pressure transducer 34 and configured to insert and remove the pressure transducer 34 from respective ones of the cooling holes. The manipulator 68 may comprise a robotic arm or other automation means.

For the arrangement shown in FIG. 3, the system 60 further includes at least one pressure sensor 28 for measuring the pressure within the plenum 26 and at least one temperature sensor 28 for measuring the temperature of the fluid within the plenum. For the illustrated arrangement, the processor 22 is operatively connected to the pressure and temperature sensors 28, to the pressure transducer 34 and to the flow meter 24. According to a more particular embodiment, the processor 22 is further configured to normalize the measured mass flow rate, pressure and temperature values to standard conditions and to compare the standardized mass flow rate, pressure and temperature values to respective baseline values to determine whether the component 2 meets a desired specification.

Beneficially, thermal inspection system 60 may be fully automated and hence faster than current inspections systems, with improved accuracy. Additionally thermal inspection system 60 allows an operator to perform other tasks, thereby increasing production throughput, while optionally creating an archive of all inspected components. Holes that are identified as needing rework can be automatically sent via network communication to the appropriate machine without an operator needing to tell the machine which hole needs to be reworked, thereby saving considerable operator time.

In addition, the thermal inspection system 60 offers potential cost and productivity savings for production shops for inspecting gas turbine components in regards to airflow design specifications and open hole inspection. Savings may be realized in the reduction of equipment expenditures and labor costs. Infrared (IR) pin-check eliminates laborious and manual pin-checking and visual waterflow inspections. Operators normally spend 5-10 minutes inspecting a single component. With the automation of IR pin-check, that time can be reallocated to other production areas.

Other benefits of thermal inspection system 60 include the fact that the IR pin-check method provides a quantitative measurement to the openness of a hole, whereas the pin-check and water flow operations are qualitative and subject to operator discretion. In addition, the IR pin-check readings may be stored electronically, whereas the pin-check and waterflow typically are not used to create a database to monitor inspection and manufacturing quality.

Although only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A system for thermal inspection of a component having at least one cooling hole, the system comprising:
   a fluid source configured to supply a warm flow and a cool flow, indirectly or directly, to at least one internal passage of the component;
   an imager configured to capture a time series of images corresponding to a transient thermal response of the component to the warm and cool flows, wherein the thermal response corresponds to a plurality of intensity or temperature values for an external surface of the component;
   at least one flow meter configured to measure the warm and cool flows supplied to the component; and
   a processor operably connected to the imager and configured to:
   determine the transient thermal response of the component around a transition time interrogating a second derivative of the intensity or temperature values with respect to time around the transition time, wherein the flow supplied to the component switches from the warm flow to the cool flow at the transition time, and
   compare the transient thermal response around the transition time with one or more baseline values or with an acceptable range of values by comparing the second derivative of the intensity or temperature values with the respective baseline value or with the respective acceptable range of values, to determine if the component meets a desired specification.

2. The system of claim 1, wherein each of the images corresponds to a plurality of pixels, wherein the processor is further configured to identify respective ones of the locations of the one or more cooling holes on the external surface of the component based on the relative intensities of the pixels in the images.

3. The system of claim 2, wherein the processor is further configured to determine a minimum for the second derivative and to compare a magnitude of the minimum with the one or more baseline values or the acceptable range of values to determine if a respective cooling hole is at least partially blocked.

4. The system of claim 2, wherein the processor is further configured to determine a minimum for the second derivative and to compare a time at which the minimum occurs with the one or more baseline values or the acceptable range of values to determine if a respective cooling hole is at least partially blocked.

5. The system of claim 1, wherein each of the images corresponds to a plurality of pixels, and wherein the processor is further configured to:
compute a first derivative of the intensity or temperature values with respect to time for at least a subset of the pixels;
normalize the first derivative of the intensity or temperature values with respect to time for the subset of the pixels; and
use the normalized first derivative to compute the second derivative of the intensity or temperature values with respect to time, such that the second derivative is interrogated around the transition time at which the flow switches from the warm to the cool flow.

6. The system of claim 5, wherein the processor is further configured to identify respective ones of the locations of the one or more cooling holes on the external surface of the component based on the relative intensities of the pixels in the images, and wherein the subset of the pixels selected for computation of the first derivatives correspond to the locations of the cooling holes.

7. The system of claim 6, wherein the processor is further configured to determine a minimum for the second derivative and to compare a magnitude of the minimum with the one or more baseline values or the acceptable range of values to determine if a respective cooling hole is at least partially blocked.

8. The system of claim 6, wherein the processor is further configured to determine a minimum for the second derivative and to compare a time at which the minimum occurs with the one or more baseline values or the acceptable range of values to determine if a respective cooling hole is at least partially blocked.

9. The system of claim 1, further comprising a plenum and at least one pressure sensor, wherein the fluid source supplies the warm and cool flows to the plenum, wherein the at least one flow meter and the at least one pressure sensor are configured to measure the warm and cool flows and pressures supplied to the plenum, and wherein the plenum is in fluid communication with at least one internal passage of the component.

10. The system of claim 1, wherein the imager comprises an infrared camera.

11. The system of claim 1, further comprising at least one manipulator for manipulating at least one of a relative position and a relative orientation of the imager and the component.

12. The system of claim 11, wherein the component has more than one cooling hole, and wherein the manipulator is configured to change an angle of the relative orientation of the imager and the component for inspecting different ones of the cooling holes.

13. The system of claim 11, wherein the manipulator is configured to change the relative position of the imager and the component to adjust the focal point of the imager within a respective cooling hole.

14. The system of claim 1, wherein the component has more than one cooling hole, and wherein the processor is further configured to identify a location of any of the cooling holes that do not meet the desired specification.

15. A system for thermal inspection of a component having a plurality of cooling holes and a plurality of internal passages, the system comprising:
a plenum in fluid communication with at least one of the internal passages of the component;
a fluid source configured to supply a warm flow and a cool flow to the plenum;
at least one flow meter configured to measure a mass flow rate for the warm and cool flows supplied to the plenum;
an imager configured to capture a time series of images corresponding to a transient thermal response of the component to the warm and cool flows, wherein the thermal response corresponds to a plurality of intensity or temperature values for an external surface of the component;
a plurality of actuated air flow stops configured to selectively interrupt the fluid communication between the plenum and respective ones of the internal passages; and
a processor operably connected to the imager and configured to:
determine the transient thermal response of the component around a transition time, wherein the flow supplied to the component switches from the warm flow to the cool flow at the transition time, and
compare the transient thermal response around the transition time with one or more baseline values or with an acceptable range of values to determine if the component meets a desired specification.

16. The system of claim 15, wherein the processor is configured to determine the transient thermal response by interrogating a second derivative of the intensity or temperature values with respect to time around the transition time, and
wherein the processor is configured to perform the comparison by comparing the second derivative of the intensity or temperature values with the one or more baseline values or with the acceptable range of values to determine if the component meets the desired specification.

17. The system of claim 15, wherein each of the images corresponds to a plurality of pixels, wherein the processor is further configured to identify respective ones of the locations of the one or more cooling holes on the external surface of the component based on the relative intensities of the pixels in the images.

18. The system of claim 15, further comprising:
at least one pressure sensor for measuring the pressure within the plenum; and
at least one temperature sensor for measuring the temperature of the fluid within the plenum,
wherein the processor is operatively connected to the pressure and temperature sensors and to the at least one flow meter, and wherein the processor is further configured to determine a flow rate though at least one of the internal passages based on the pressure and temperature within the plenum and on the mass flow rate measured by the at least one flow meter.

19. The system of claim 15, further comprising at least one pressure transducer configured to block a respective one of the cooling holes and to measure a static pressure at the cooling hole.

20. The system of claim 19, wherein the processor is operably connected to the pressure transducer and is further configured to compare the measured static pressure to a baseline value to determine whether the respective cooling hole is operable.

21. The system of claim 19, further comprising at least one manipulator operatively connected to the at least one pressure transducer and configured to insert and remove the pressure transducer from respective ones of the cooling holes.

22. The system of claim 19, further comprising:
at least one pressure sensor for measuring the pressure within the plenum; and
at least one temperature sensor for measuring the temperature of the fluid within the plenum,
wherein the processor is operatively connected to the pressure and temperature sensors, to the pressure transducer and to the flow meter, and wherein the processor is further configured to normalize the measured mass flow rate, pressure and temperature values to standard conditions and to compare the standardized mass flow rate, pressure and temperature values to respective baseline values to determine whether the component meets a desired specification.

* * * * *